United States Patent [19]

Spector

[11] Patent Number: 4,882,149
[45] Date of Patent: Nov. 21, 1989

[54] PHARMACEUTICAL DEPOT PREPARATION

[75] Inventor: Myron Spector, Atlanta, Ga.

[73] Assignee: Ed. Geistlich Sohne A.G. fur Chemische Industrie, Lucerne, Switzerland

[21] Appl. No.: 248,302

[22] Filed: Sep. 21, 1988

Related U.S. Application Data

[63] Continuation of Ser. No. 6,557, filed as PCT GB86/00310 on Jun. 3, 1986, published as WO86/07265 on Dec. 18, 1987, abandoned.

[30] Foreign Application Priority Data

Jun. 4, 1985 [GB] United Kingdom ............... 8514055

[51] Int. Cl.⁴ ............................................ A01N 25/00
[52] U.S. Cl. .................... 424/425; 424/426; 424/491; 424/499; 514/2; 514/222.2; 604/891.1; 604/50; 623/16; 623/18; 623/66
[58] Field of Search ............... 424/425, 426, 491, 499; 514/2, 222.2; 604/890, 891; 623/16, 18, 66

[56] References Cited

U.S. PATENT DOCUMENTS

| 4,322,398 | 3/1982 | Reiner et al. | 424/425 |
| 4,587,268 | 5/1986 | Pfirrmann | 514/222 |
| 4,610,692 | 9/1986 | Eitenmuller et al. | 424/423 |

FOREIGN PATENT DOCUMENTS 0147021 3/1985 European Pat. Off.

Primary Examiner—John Kight
Assistant Examiner—Samuel A. Acquah
Attorney, Agent, or Firm—Bernard, Rothwell & Brown

[57] ABSTRACT

Pharmaceutical depot preparation for implantation into base tissue comprising natural bone mineral from which the naturally associated fat and bone-proteins have been removed whereby said bone is sterile and non-allergenic, said bone mineral having absorbed thereon and/or adsorbed therein one or more physiologically active substances. The physiologically active substance is advantageously an antibiotic or taurolidine or tauraltam or a protein or polypeptide assisting bone regeneration.

9 Claims, No Drawings

PHARMACEUTICAL DEPOT PREPARATION

This is a continuation of application Ser. No. 6,557, filed as PCT GB86/00310 on Jun. 3, 1986, published as WO86/07265 on Dec. 18, 1986, now abandoned.

This invention relates to pharmaceutical depot compositions comprising natural bone mineral containing adsorbed and/or absorbed drugs such as antibacterial-antitoxin agents, polypeptides and proteins.

The predictable, controlled delivery of selected molecules into specific sites in the body is presently accomplished by injection or incorporation of the molecules into a "drug delivery system" which is implanted into that site. Introduction of agents into a specific site over a requisite time period is often impossible by injection or infusion. Materials previously proposed to release preadsorbed agents into bone tissue include a variety of resorbable and nonresorbable polymers including polylactic acid and polymethylmethacrylate, and synthetic calcium phosphates including the mineral hydroxyapatite and the compound tricalcium phosphate. Depot compositions based on tricalcium phosphate are described, for example, in German OLS Nos. 2807132, and 2843963 and EP No. 87662. However, these materials are inadequate because of limited adsorption/absorption capacity, untimely resorption, incompatibility with bone regeneration, and/or inability to release sufficient calcium along with the selected agent. Previously proposed natural bone materials that contain organic matter are ineffective because the organic material interferes with adsorption of the molecule onto the bone mineral, can elicit an immunogenic response, interferes with the resorption of the implant, and interferes with the bone regeneration process.

We have found that it is possible to prepare and apply a natural bone mineral substance which overcomes some of the deficiencies of previously employed delivery systems by adsorbing and/or absorbing selected molecules in sufficient quantities in vitro and releasing same in a predictable fashion in vivo while facilitating bone regeneration. The properties of the natural bone mineral substance to adsorb molecules, release these in vivo and, facilitate bone regeneration are related to the absence of organic matter and related to the composition, structure, and morphology of the inorganic phase of bone, in particular its porosity and crystallinity.

Natural bone mineral comprises hydroxyapatite-like crystallites with a particular degree of crystallinity, habit and size (irregular plate-like morphology, 5–20 nm in thickness and 25–100 nm in length, (typically 14 nm with AA-axis direction and 3.4 nm in the Co-axis direction), and surface chemistry resulting from the calcium to phosphate ratio (37.5–38.0% calcium and 15.5–19.0% phosphorus). Also present in the natural bone mineral are small amounts of noncrystalline entities and other calcium phosphate crystalline phases including the minerals Brushite and Whitlockite, and octa-calcium phosphate. The inorganic phase of bone contains porosity including ultrastructural interstices (10–100 nm) between the crystallites occurring naturally and produced by removal of the organic phase, and microscopic spaces (1–20 microns) including osteocyte lacunae, canaliculi, vascular channels, volkman's canals, and the canals of haversian systems (100–500 nm). The specific surface area, which is a measure of porosity is in the range 50 to 100 $m^2/gm$ as determined by mercury porosimetry. The crystallinity of bone mineral can be characterized by X-ray diffraction and the porosity and crystallite morphology and size by electron microscopy. Small amounts of nonapatitic crystallites can be detected by thermogravimetric analysis. We have found that the composition and structure of natural bone mineral cannot be duplicated by products formed in vitro or by naturally occurring hydroxyapatites prepared previously.

The composition and structure of bone mineral yield a substance with a very large surface area, highly chemically active surface, and ultra- and microscopic-porosity. These features combine to yield unique adsorption and resorption properties which provide high efficiency in adsorbing and absorbing drug molecules in vitro and releasing these in a predictable fashion in vivo.

We have found that an improved bone mineral product can be obtained by rigorously removing fat and bone-proteins using appropriate solvents. The new material is an excellent adsorbent/absorbent for active molecules and has improved resorption characteristics.

According to one feature of the present invention we provide pharmaceutical depot preparations for implantation into bone tissue comprising natural bone mineral from which the naturally associated fat and bone-proteins have been removed whereby said bone is sterile and non-allergenic, said bone mineral having adsorbed thereon and/or absorbed therein one or more physiologically active substances.

The bone mineral material according to the invention may be used to fill congenital, surgical or traumatic defects, for example osteitis cavities or other surgical sites such as defects arising from surgical removal of cysts and tumours, formation of cementless prostheses in joint replacement, grouting between bone fragments in complex fractures, filling defects in maxillo-facial or craniofacial surgery, filling defects in dental or oral surgery, e.g. filling extraction sockets, alveolar ridge augmentation and filling periodontal defects and other defects in the mandible or maxilla.

In general, the preparations according to the invention will consist simply of the bone mineral and physiologically active substance, without any other substances which may interfere with drug release or mineral resorption. The porous structure of the material facilitates absorption of the physiologically active substance and also its release in vivo.

The bone mineral will normally be in particulate form, for example in the form of particles of average diameter 0.1 to 3 mm, preferably 0.25 to 2 mm, in the case of cortical bone. Larger particles may be appropriate in the case of spongiosa bone. Thus, the microporous structure of the bone mineral is maintained as well as the microcrystalline surface.

Physiologically active substances which may be incorporated into the compositions are preferably at least partially water-soluble and include antibacterial substances such as antibiotics, e.g. penicillins, cephalosporins, aminoglycosides etc., sulphonamides and, in particular, condensation products of formaldehyde with taurinamide or N-substituted taurinamide. The latter compounds may be represented by the formula

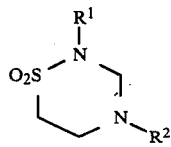

where $R^1$ is hydrogen or a $C_{1-4}$ alkyl group and $R^2$ is hydrogen or a group of the formula

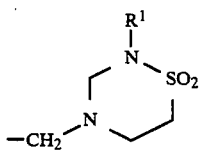

where $R^1$ has the above meaning.

The compound of formula (I) in which $R^1$ and $R^2$ are both hydrogen is taurultam while the compound in which $R^1$ is hydrogen and $R^2$ has the formula (II) is taurolidine. These compounds act as methylol transfer agents and are effective not only in destroying both gram negative and gram positive bacteria but also in inactivating both endotoxins and exotonins produced by the bacteria.

Other useful physiologically active substances include proteins and polypeptides capable of assisting bone regeneration especially non-collagenous proteins derived from bone matrix and bone cells. These include mitogenic factors such as skeletal growth factor and morphogenic and angiogenic factors.

The bone mineral may be prepared by extraction of natural bone with solvents and/or proteolytic agents. Bovine bone is preferred, especially that from the large bones such as the femur and tibia and other limb-bones. Cortical bone is preferred but spongiosa bone may be used.

The bone is preferably first comminuted to a suitable size and then subjected to extraction techniques such as those described by S. Gabriel (Hoppe-Beyler's Z. Physiol. Chem. 18(1984) 257, J.B. Williams et al (Science 199 (1954) 771), F. L. Loose et al (Nature, 177 (1956) 1032), H. Stegemann et al (Hoppe-Seyler's Z. Physiol. Chem. 320 (1960) 272),. Armour and Co. USP 2968593), R. Kershaw (The Pharm. J. (1963) 537) and C. W. Skinner et al (Calc.Tiss.Res. 10 (1972) 257.

Thus, for example, fats may be removed using one or more conventional fat solvents such as ethers, e.g. diethyl ether; ketones e.g. acetone; or hydrocarbons or halogenated hydrocarbons e.g. heptane or methylcylcohexane or toluene.

It may be advantageous to remove an extractant such as toluene by an intermediate extraction with a water miscible solvent such as ethanol before proceeding further. Collagen material may be dissolved using proteolytic agents such as bases e.g. potassium hydroxide in glycerol, or organic basis such as amines, e.g. ethylene diamine, or amides such as formamide, preferably at elevated temperatures, e.g. above 100° C. Such agents are preferably water-miscible to facilitate removal by water washing. We have found that fat may often be removed simultaneously with protein in a single extraction. Especially good results have been obtained using bone extracted with refluxing ethylene diamine.

Extraction may advantageously be continued at each stage, if necessary with changes of solvent, until no further material is extracted, e.g. for periods up to one or two weeks. It may be advantageous to comminute further after initial protein extraction, since the bone is more readily fractured at that stage than before extraction. After extraction, excess solvents are rigorously removed e.g. by evaporation and/or, where suitable, water washing. Water washing may for example be effected for long periods at 100° C. to ensure that all the solvent and dissolved substances are removed.

The material is normally subjected to a drying step. It may be convenient to sterilise the material at this stage, e.g. by heat treatment. Absorption and/or adsorption of the physiologically active substance is preferably effected by immersing the treated bone mineral in an aqueous solution thereof preferably under sterile conditions. The concentration of the active substance is preferably relatively high to facilitate adsorption and/or absorption and will depend in part on the solubility of the active material.

The following example is given by way of illustration only:

Bovine femur bones were boiled in hot water until clean, comminuted to a particle size of 5 to 10mm. and extracted under reflux with toluene for 24 hours in a Sohxlet apparatus. The material was further extracted with ethanol to remove toluene and then extracted at 118° C. with an azeotropic mixture of ethylene diamine and water (85:15) for 8 days, with several changes of solvent until substantially no further organic material was extracted. After extraction the material was washed with water at 100° C. for 10-14 days with frequent changes of water. The product was then air dried at 100° C.

The dried product was further comminuted to an average particle size of 0.2 to 2 mm and sterilized in the autoclave.

The sterilised material was suspended in a sterile 2% solution of taurolidine for 30 minutes, filtered, sterile-dried and sterile packed.

The bone mineral material has been implanted in non-primates and has shown little evidence of resorption after 100 days as seen from the absence of osteocysts on the surface of the particles. The implanted particles retained their original form although many surfaces were enveloped by new bone directly in contact therewith.

I claim:

1. Pharmaceutical depot preparations for implantation into bone tissue comprising natural bone mineral from which the naturally associated fat and bone-proteins have been removed whereby said bone is sterile and non-allergenic, said bone mineral having adsorbed thereon and/or absorbed therein one or more physiologically active substances.

2. Preparations as claimed in claim 1 in the form of particles of average diameter 0.1 to 3 mm.

3. Preparations as claimed in claim 1 or claim 2 in which the physiologically active substance is an antibiotic or a condensation product of formaldehyde with taurinamide or an N-$C_{1-4}$ alkyl-taurinamide.

4. Preparations as claimed in claim 3 in which the physiologically active substance is taurolidine or taurultam.

5. Preparations as claimed in claim 1 or 2 in which the physiologically active substance is a protein or polypeptide capable of assisting bone regeneration.

6. A method of preparing a pharmaceutical depot preparation for implantation into bone tissue wherein natural bone is subjected to extraction of fat and bone protein therefrom whereby said bone is sterile and non-allergenic whereafter one or more physiologically active substances is adsorbed thereon or absorbed therein.

7. A method of filling congenital, surgical or traumatic defects in bone whereby said defect is filled with a preparation as claimed in claim 1.

8. A method as claimed in claim 1 for filling osteitis cavities, defects arising from surgical removal of cysts and tumours, maxillo-facial or cranio-facial surgery or dental or oral surgery, for formation of cementless prostheses in joint replacement or for grouting bone fragments in complex features.

9. A bone material from which fat and bone-protein have been removed for use in the formation of preparations as claimed in claim 1.

* * * * *